US00PP10952P

United States Patent [19]

Kuijf

[11] Patent Number: Plant 10,952

[45] Date of Patent: Jun. 8, 1999

[54] CLEMATIS PLANT NAMED 'KUGOTIA'

[76] Inventor: H. J. M. Kuijf, Mennonjetenbuut 116A, 1427 B.C. Ulthoom, Netherlands

[21] Appl. No.: 08/879,956

[22] Filed: Jun. 20, 1997

[51] Int. Cl.[6] ..... A01H 5/00

[52] U.S. Cl. ..... Plt./228

[58] Field of Search ..... Plt./54.1, 228

[56] References Cited

PUBLICATIONS

UPOV "*Clematis serratifolia*—Kugotia" AU PBR 97106, 1998.

Huxley et al. (Eds.) "Clematis", The New RHS Dictionary of Gardening, The Stockton Press New York. vol. 1 pp. 640–652, 1992.

*Primary Examiner*—Howard J. Locker
*Assistant Examiner*—Melissa L. Kimball
*Attorney, Agent, or Firm*—Christie, Parker & Hale, LLP

[57] ABSTRACT

A Clematis plant variety producing deep yellow flowers.

1 Drawing Sheet

BACKGROUND OF THE INVENTION

The new variety resulted from seeds harvested from a cross of 'Golden Harvest' and an unknown variety which was being grown among a large collection of various Clematis varieties. The seed was planted and cultivated. One of the seedlings was selected because of its particularly desirable attributes. Asexual propagation of this seedling resulted in the new variety 'Kugotia' which is described herein. It is not possible to know the parents of the new variety since it could be a self pollination of the aforementioned cross of 'Golden Harvest' or a cross pollination from a neighboring plant. The varieties 'Golden Harvest' and 'Helios' (discussed below) are not patented.

SUMMARY OF THE INVENTION

Among the novel characteristics possessed by the new variety which distinguish it from its parent and all other varieties of which I am aware are its attractive flowers borne on a hardy climbing plant with annual stems of about 2 to 3 m. long.

Asexual reproduction by vegetative cuttings as performed in Azusa, Calif., shows that the foregoing and other distinguishing characteristics come true to form and are established and transmitted through succeeding propagations.

COMPARISON WITH PARENT AND OTHER VARIETIES

The new variety is similar in appearance to 'Golden Harvest' but differs in having larger flowers which are of darker color and with the tepal being pubescent inside. The shape of the flower when fully opened is similar to the variety 'Helios' but differs in having darker colored filaments.

BRIEF DESCRIPTION OF ILLUSTRATION

The accompanying illustration shows typical specimens of the vegetative growth and flowers of the new variety depicted in color as nearly true as is reasonably possible to make the same in a color illustration of this character.

DESCRIPTION OF THE NEW VARIETY

Parentage: Chance seedling of the Clematis variety 'Golden Harvest'.

The following is a detailed description of the new variety from specimens grown in Azusa, Calif. The color terminology used in according with The Royal Horticultural Society Colour Chart (R.H.S.C.C.), and refers to the plate numbers in the aforementioned color chart. Phenotypic expression may vary depending on light, environmental and cultural conditions.

The botanical name of the new variety is *Clematis serratifolia* 'Kugotia'. The flowers nod and are bisexual. They first open campanulate but later spread up to about 7 cm. across. The receptacle is green and the bud is almost orbicular and greenish-yellow. There are four tepals of deep yellow coloring on both sides.

1. Flower:
   - A. *Flowering time.*—July to October.
   - B. *Inflorescence.*—Solitary, axillary on young shoots, the stems have no terminal flower, sometimes with undeveloped side buds. Peduncle: Peduncle about 1 to 3 cm. long, sparsely hairy, green flushed with purple. Pedicel: About 6 to 18 cm. long, sparsely hairy, green to purple. Bud: Almost orbicular, greenish-yellow, at first upright but very quickly nodding, color near 5A with green tint; green bud near 154A prior to opening; no bracts. Flower: Bisexual, nodding, first open campanulate but later spreading up to about 7 cm. across, just a bit sweet fragrance when young; color of flower just opening near 6A.
   - C. *Tepals.*—4, deep yellow on both sides. Base: Greenish, when out of flower a bit more orange; length about 3 to 3.7 cm. (average 3.5 cm.); width about 1 to 1.7 cm. (average 1.5 cm.); elliptic;, rather thick. Apex: Acute-acuminate and bends outwards, inside sparsely pubescent, outside glabrous. Margin: Short tomentum. Color: Near 12A to 9A on both sides, near 13A to 13B when at the end of the flowering stage.
   - D. *Stamens.*—Filaments: Rather equal in length up to about 1.3 cm. long and 0.1 cm. wide; linear-lanceolate dark purple near 79A to 79B but base greenish, hairy at the lower half but base itself glabrous. Anthers: About 0.3 to 0.4 cm. long, linear-oblong and pale purple; pollen is grey-cream; connective is dark purple, glabrous, obtrusely elongated.
   - E. *Pistil.*—Initially shorter than the stamens but in full flower quickly elongating and becoming much longer than the stamens. Ovary: Hairy, style white plumose. Stigma: Yellow and glabrous. Style: Up to about 3.5 cm long, plumose with white long hairs about 0.4 cm but shorter towards stigma; stigma glabrous, black when dried, slightly hooked.

F. *Bracts.*—Present, leaflike but simple, ovate, up to about 3.5 cm. long and about 2.5 cm. wide or much less. Apex: Acuminate. Base: Cuneate-obtuse, margin with 1 to 2 acute teeth and usually with an obtuse-acute lobe at the base on both sides, glabrous on both sides.

Plant:

A. *Leaf.*—Compound pinnate. (1) Leaflets: About 7 to 9, the upper is simple, the lower pairs usually ternate or sometimes simple and cleft; mature foliage near 137A, new foliage near 143B. Terminal leaflets: Lanceolate, up to about 6 cm. long and about 2 cm. wide or less. Apex: Acuminate. Base: Cuneate. Margin: Serrate with up to about 5 acute teeth at about the middle, sometimes lobed at the base. Side leaflets: Ovate, up to about 3 cm. long and about 1 to 5 cm wide or less. Apex: Acute. Base: Cuneate-obtuse. Margin: Up to about 3 acute teeth, sometimes lobed at the base, normal green and flushed with purple glabrous on both sides; petiole up to about 3 cm. long or less, sometimes curling, glabrous, greenish-purple. (2) Petiole: Up to about 7 cm long, glabrous, near 145B especially at upper side, base a bit connate and with a few short hairs. (3) Stem: Shaded side—near 145B; sun side near 53A (overlaid or muted by tomentum); color streaked but not continuous on the stem.

B. *Habit.*—A hardy climber with annual stems about 2 to 3 m. long, young growing tip hairy, becoming glabrous; internodes up to about 17 cm. long and glabrous, greenish-purple; distinct 6 ribs which are usually purple colored at the upper part of the stems, otherwise green colored.

3. Fruit:

A. *Head.*—Up to about 5 cm across, shiny white, upright.

B. *Achene.*—With long hairs especially towards style.

4. Winter hardiness: Zone 5, −20° to −10° F.

5. Disease resistance: Average disease resistance similar to other Clematis.

I claim:

1. A new and distinct Clematis plant of the variety substantially as shown and described.

* * * * *

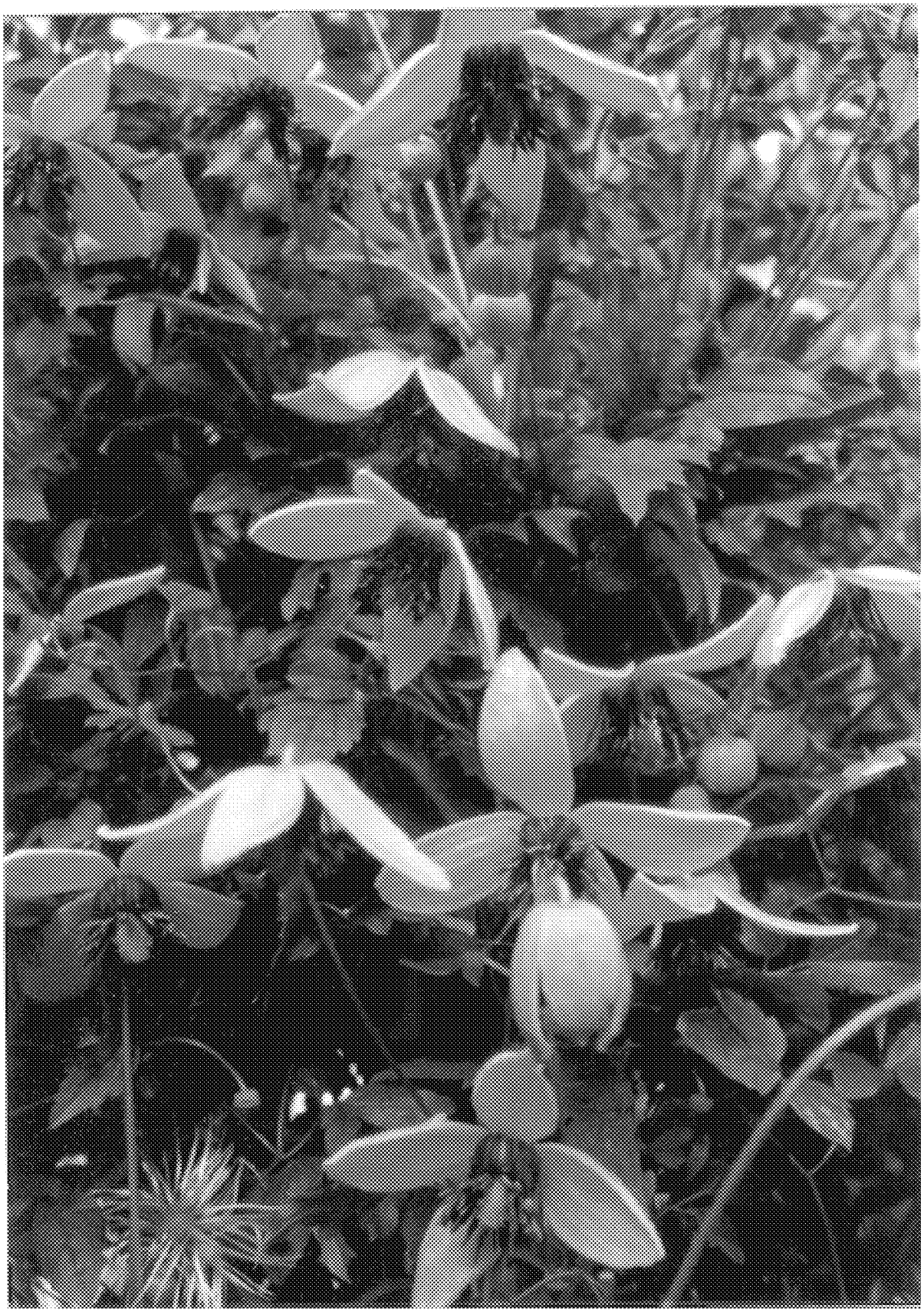

UNITED STATES PATENT AND TRADEMARK OFFICE

CERTIFICATE OF CORRECTION

PATENT NO. : Plant 10,952
DATED : June 8, 1999
INVENTOR(S) : H. J. M. Kuijf

It is certified that error appears in the above-identified patent and that said Letters Patent is hereby corrected as shown below:

Column 2, line 1, change "according" to -- accordance --.
Column 2, line 44, after "elongated." insert
-- Styles (anthers and filaments): About 1.5 cm. --.

Signed and Sealed this

Tenth Day of April, 2001

*Attest:*

Nicholas P. Godici

NICHOLAS P. GODICI

*Attesting Officer*

*Acting Director of the United States Patent and Trademark Office*